United States Patent [19]

Takano et al.

[11] Patent Number: 5,352,606
[45] Date of Patent: Oct. 4, 1994

[54] FREEZE RESISTANT BAKERS' YEAST

[75] Inventors: Hiroyuki Takano; Akihiro Hino, both of Tsukuba; Hisanori Endo, Mishima; Nobuaki Nakagawa, Tagata; Akio Sato, Mishima, all of Japan

[73] Assignee: Asahi Kasei Kogyo Kabushiki Kaisha, Osaka, Japan

[21] Appl. No.: 808,586

[22] Filed: Dec. 17, 1991

Related U.S. Application Data

[63] Continuation-in-part of Ser. No. 757,692, Sep. 11, 1991, abandoned, which is a continuation of Ser. No. 491,248, Mar. 8, 1990, abandoned.

[30] Foreign Application Priority Data

Mar. 14, 1989 [JP] Japan ..................... 1-59638

[51] Int. Cl.⁵ ............ C12N 1/18; C12N 15/04; A23L 1/105
[52] U.S. Cl. .............. 435/255.2; 435/172.1; 435/942; 426/62; 426/18; 426/60; 426/19; 426/549; 935/97
[58] Field of Search .............. 435/255, 256, 172.2, 435/942; 935/97; 426/60, 62, 549, 19

[56] References Cited

U.S. PATENT DOCUMENTS 4,318,929 3/1982 Clement et al. ............... 426/62
4,547,374 10/1985 Nakatomi et al. ............ 435/256
4,643,901 2/1987 Jacobson et al. ............. 435/256
4,680,182 7/1987 Kawai ........................ 426/62
4,973,560 11/1990 Jacobson et al. ............. 435/256

FOREIGN PATENT DOCUMENTS 0196233 10/1986 European Pat. Off. .
59-25584 6/1984 Japan .
59-48607 11/1984 Japan .
59-203442 11/1984 Japan .
60-15308 4/1985 Japan .
62-208273 9/1987 Japan .

OTHER PUBLICATIONS

Creuger et al., "Strain Development," In Biotechnology a Textbook of Industrial Microbiology, Oldenbourg Verlag, Müchen, 1989 pp. 9–58.
Spencer et al., "Genetic Manipulation of Non-Conventional Yeasts by Conventional and Non-Conventional Methods," J. Basic Microbiol., 28 (5) pp. 321–333 1988.

*Primary Examiner*—Marian Knode
*Attorney, Agent, or Firm*—Darby & Darby

[57] ABSTRACT

A diploid hybrid bakers' yeast belonging to *Saccharomyces cerevisiae* having at least strong fermentative ability of non-sugar bread dough and strong freeze-resistance and frozen bread dough containing the same are provided.

9 Claims, 3 Drawing Sheets

FREEZE RESISTANT BAKERS' YEAST

This is a continuation-in-part application of Ser. No. 07/757,692 filed on Sep. 11, 1991, now abandoned, which is a continuation application of Ser. No. 07/491,248 filed on Mar. 8, 1990, now abandoned.

FIELD OF THE INVENTION

The present invention relates to a diploid hybrid strain characterized by at least having strong fermentative ability of "non-sugar bread dough" (hereinafter may be referred to as "non-sugar dough") and strong freeze-resistance and also relates to "frozen bread dough" (hereinafter may be referred to as "frozen dough") containing at least the hybrid strain and a dough composition. Furthermore, this invention relates to production of a variety of bread by using the frozen dough.

BACKGROUND OF THE INVENTION

Recently, frozen dough for bread has become very attractive to the baking industry because it has the following great advantages; i.e., (1) it may be useful in the supply of fresh-baked bread; and (2) it has vast merits for solving industrial productivity problems by shortening the baking process (savings of labor) and reducing the need for a night shift. Frozen dough is produced by kneading and fermenting materials for bread, keeping the material under freezing at around $-20°$ C. The frozen dough is subjected to baking after, if necessary, proofing. Common bakers' yeast is so likely damaged by fermentation prior to freezing that the use of yeast is limited to a case where the dough is enriched with a relatively large amount of materials such as sugar, fat, egg, milk products, etc. is not subjected to fermentation or subjected to fermentation for only a short time prior to freezing. When the dough containing common bakers' yeast which has been fermented for a short time before freezing is thawed and baked immediately after proofing, it cannot be sufficiently baked so that it causes some problems such that flavor and taste of bread may be deteriorated. A process wherein the frozen dough is thawed and subjected to proofing requires a long time for baking, so that the purpose of frozen dough method may be lost.

Thus, there has been a demand for a kind of bakers' yeast which has a great freeze-resistance, may be hardly damaged by storage under the frozen condition after fermentation, during preparation of frozen dough. Some reports have presented kinds of yeast having freeze-resistance, i.e., *Saccharomyces rosei* (Japanese Patent Kokoku No. 59-25584), *Saccharomyces cerevisiae* FTY (Japanese Patent Kokoku No. 59-48607), *Saccharomyces cerevisiae* IAM4274 (Japanese Patent Kokai No. 59-203442). Both *Saccharomyces rosei* and *Saccharomyces cerevisiae* FTY (FRI-413) do not have strong maltose-fermentative ability and therefore, they are not suitable for use in frozen dough with the sugar content in the range of 0 to 20% by weight based on flour, i.e., from non-sugar dough to dough with a moderate sugar level. *Saccharomyces cerevisiae* IAM4274 has maltose-fermentative ability but does not show sufficient freeze-resistance in the dough with the sugar content in the range of 0 to 20% by weight based on flour, i.e., from non-sugar dough, etc. to the dough with a moderate sugar level. Size of the yeast *Saccharomyces rosei* is smaller than that of common bakers' yeasts, so that it takes a long time for separation, washing and dehydration of yeasts. The other reports have presented bakers' yeast which is suitable for the dough for lean type bread and has maltose-fermentative ability and freeze-resistance, i.e. *Saccharomyces cerevisiae* KYF110 (Japanese Patent Kokai No. 62-208273), and a fusant strain *Saccharomyces cerevisiae* 3-2-6D (Japanese Patent Kokai No. 63-294778) which is obtained by the cell fusion technique and has strong maltose-fermentative ability and enhanced freeze-resistance. However, these are not satisfactory yet.

As heretofore mentioned, there has not been obtained bakers' yeast which has strong fermentative ability and great freeze-resistance of non-sugar dough up to the dough with a moderate sugar level (up to 20% by weight based on flour), and which is appropriate for the non-sugar dough without sugar such as French bread and bread crumb or the dough for a white bread. Therefore, it has been extremely difficult to produce frozen dough for such kinds of bread.

The common bakers' yeast commercially available for non-sugar dough has a drawback on storability because of the rapid decrease of its fermentative ability under storage in the form of products, compared with the deterioration rate of ordinary bakers' yeasts having high fermentative ability of dough of a higher sugar level and middle fermentative ability of non-sugar dough, which are widely used for the bread with the sugar content in the range of 5% to 30% by weight based on flour.

SUMMARY OF THE INVENTION

After intensive study to solve the above problems, the present inventors succeeded in a diploid hybrid strain which has both at least the same fermentative ability as the common bakers' yeasts for non-sugar dough, with respect to fermentation of dough having up to moderate sugar level (sugar content; 0 to 20% by weight based on flour), and has strong freeze-resistance. The "diploid hybrid strain" is obtained by conjugation between a "haploid yeast strain" (hereinafter may be referred to as "haploid strain") obtained from germination of spores from a diploid yeast strain belonging to *Saccharomyces cerevisiae* having at least strong fermentative ability on non-sugar dough and a haploid yeast strain obtained from germination of spores from a diploid yeast strain belonging to *Saccharomyces cerevisiae* having strong freeze-resistance but such a weak fermentative ability on non-sugar dough that it is hardly used for frozen dough of lean type bread. Furthermore, they found that the diploid hybrid strain was usable as bakers' yeast for non-sugar dough up to dough with a moderate sugar level, specifically for frozen dough. High quality bread can be obtained from frozen doughs which are made with the diploid hybrid strain and have non-sugar to a moderate sugar level, for example, non-sugar dough for such as French bread and bread crumb and dough for a white bread.

Additionally, the present diploid hybrid strain shows slower reduction in fermentative ability during storage than common bakers' yeast for non-sugar dough. Thus, the diploid hybrid strain provides great advantages in terms of storage.

DETAILED DESCRIPTION OF THE INVENTION

According to the present invention, a diploid hybrid strain characterized by at least having strong fermentative ability of non-sugar dough and strong freeze-resistance, which is provided by conjugation between a haploid yeast strain obtained from germination of spores of a diploid yeast strain belonging to *Saccharomyces cerevisiae* having at least strong fermentative ability on non-sugar bread dough and a haploid yeast strain obtained from germination of spores from a diploid yeast strain belonging to *Saccharomyces cerevisiae* which has strong freeze-resistance but weak fermentative ability on non-sugar bread dough. The present invention further provides frozen bread doughs containing at least the diploid hybrid strain and a dough composition.

Figure 1:
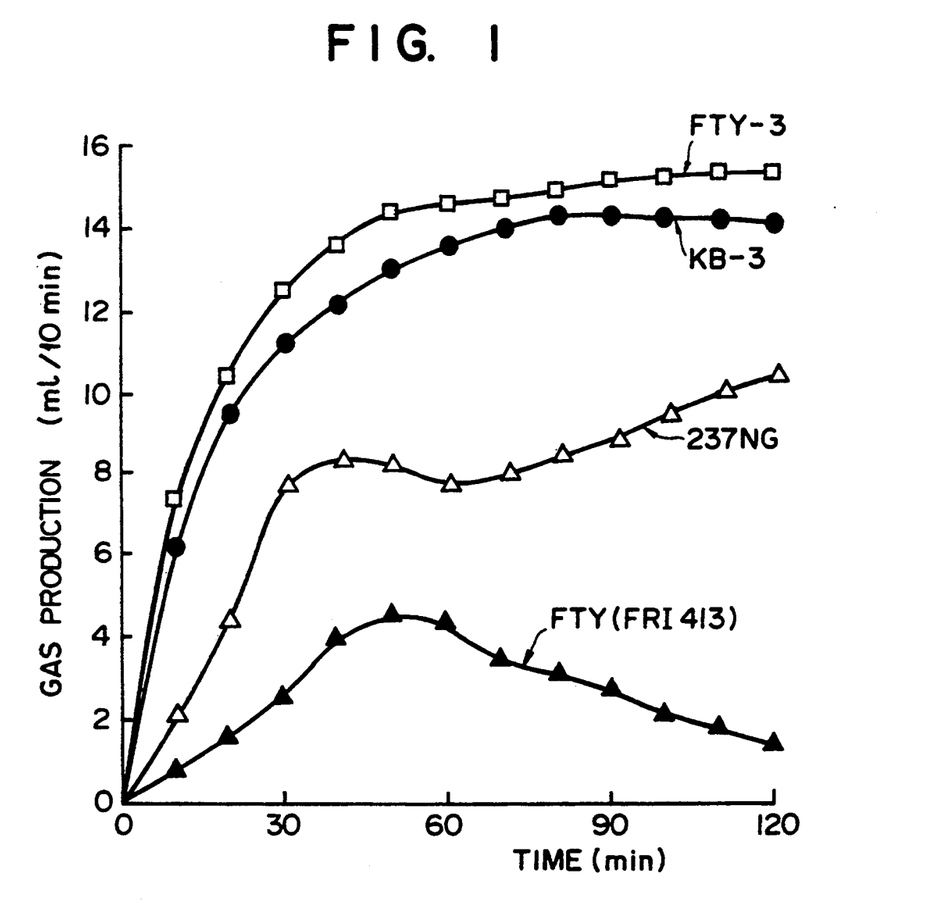
FIG. 1 shows $CO_2$ gas production as a function of the time of fermenting non-sugar dough for a yeast strain according to the invention (FTY-3) and for three comparative strains (KB-3, 237NG, FTY).
Figure 2:
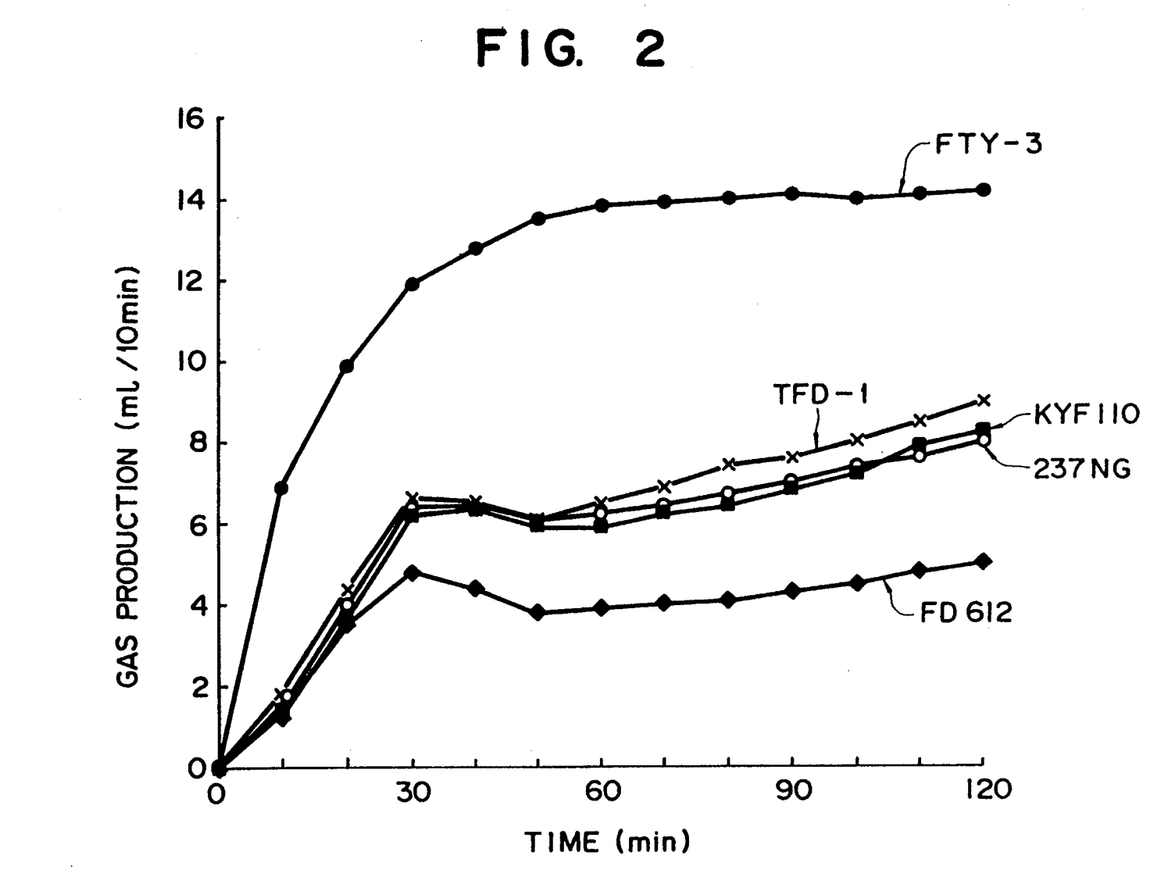
FIG. 2 shows the fermentation profile ($CO_2$ v. time) for strain FTY-3 and four comparative strains (TFD-1, KYF110, 237NG, FD612) fermented on non-sugar dough after the yeast strains had been frozen for 7 days.
Figure 3:
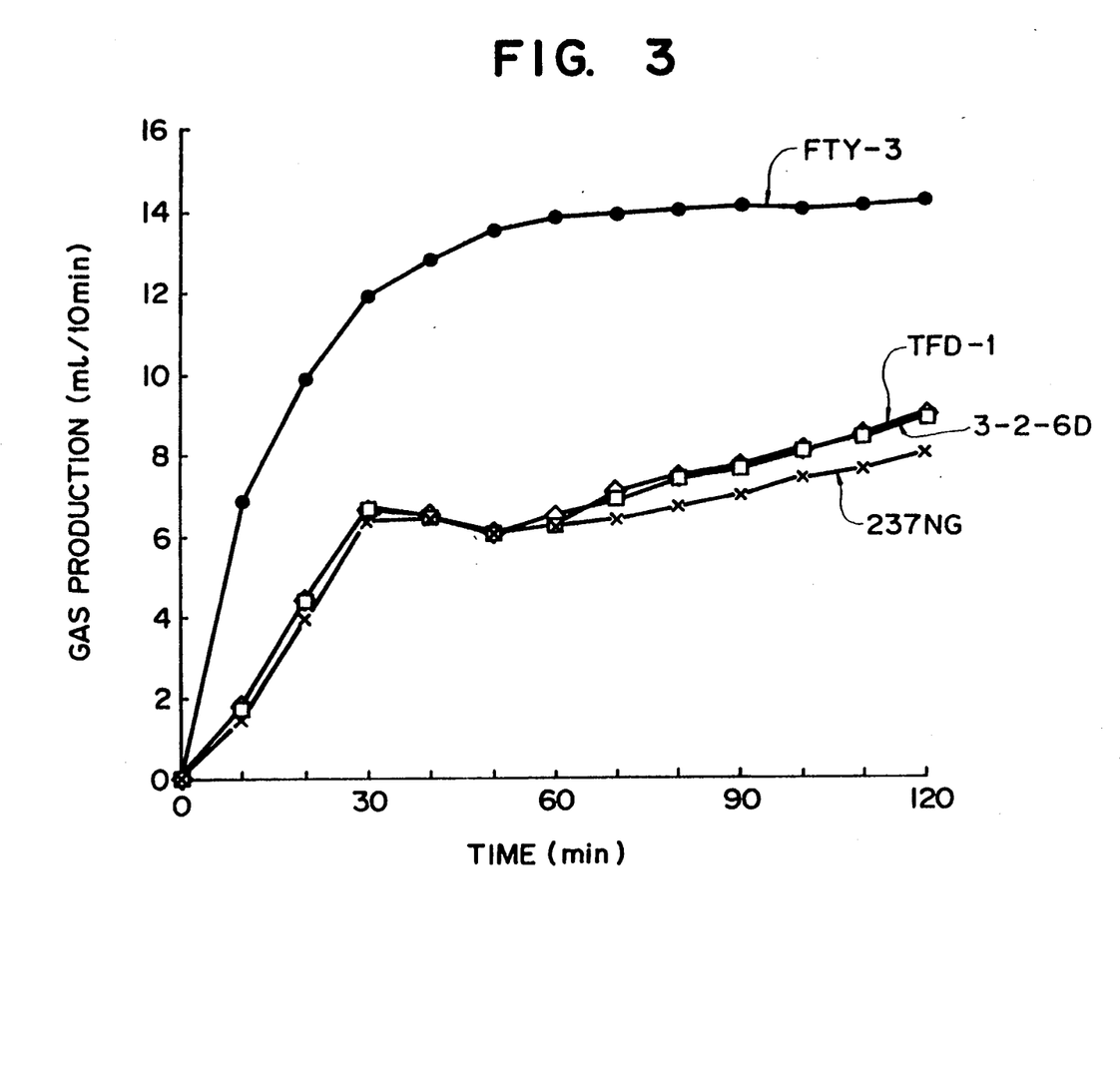
FIG. 3 shows the fermentation profile ($CO_2$ v. time) for strain FTY-3 and three comparative strains (TFD-1, 3-2-6D, 237NG) on non-sugar dough after the yeast strains had been frozen for 7 days.

In accompanying drawings, FIG. 1 shows that $CO_2$ production every 10 minutes from non-sugar dough of Example 2 mentioned below. In the drawing, marks □, ●, Δ and ▲ are for yeasts of the present diploid hybrid strain FTY-3 (FERM BP 2326), KB-3 (FERM BP 2742) or a mate for the FTY-3, 237 NG and FTY (FERM BP 2743) or a mate for the FTY-3, respectively. FIGS. 2 and 3 show the similar graphs to FIG. 1, refering to Example 10 mentioned below wherein each strain is allowed to ferment at 30° C. for 2 hours in a non-sugar dough, in which the marks ●, ■, ◆, * and ○ in FIG. 2 are for FTY-3 (present diploid hybrid strain), KFI 110, FD 612 (heretofore known hybrid strains), TFD-1 (commercially available freeze-resistant yeast strain) and 237 NG (ordinary non-freeze-resistant yeast strain) strains, respectively, and the marks ●, ■, ◆ and * in FIG. 3 are for FTY-3, 3-2-6D (heretofore known hybrid strain), TFD-1 and 237 NG strains respectively.

The diploid hybrid strain according to the present invention is obtained by conjugation between two parent strains, i.e. a haploid strain from germination of spores from a diploid yeast strain belonging to *Saccharomyces cerevisiae* which has at least strong fermentative ability of non-sugar dough and a haploid strain from germination of spores from a diploid yeast strain belonging to *Saccharomyces cerevisiae* which has strong freeze-resistance. One such diploid hybrid strain is *Saccharomyces cerevisiae* FTY-3 (FERM BP-2326) deposited at the Agency of Industrial Science and Technology, the Fermentation Research Institute, 1-3, Higashi 1-chrome, Tsukuba-shi, Ibaraki-ken 305 Japan on Mar. 7, 1989 under the terms of the Budapest Treaty.

One of the parent strains, a diploid yeast strain belonging to *Saccharomyces cerevisiae* having at least strong fermentative ability of non-sugar dough, may be any bakers' yeast for non-sugar dough commercially available in the market or any yeast strains which exhibit equivalent fermentative ability to the yeast above but has weak freeze-resistance. One example thereof is *Saccharomyces cerevisiae* KB-3 (FERM BP 2742; product name, "45 Red Yeast"; manufactured by Toyo Jozo Company, Ltd.) deposited at the above depository on Jan. 24, 1990 under the terms of the Budapest Treaty.

Another parent diploid yeast strain belonging to *Saccharomyces cerevisiae* which has at least strong freeze-resistance, may be any yeast strains which have equivalent degree of freeze-resistance to that of the yeasts used in frozen rich bread dough and which exert weak fermentative ability of non-sugar dough but strong freeze-resistance. One example is *Saccharomyces cerevisiae* FTY (FIJI-413) (FERM BP 2743) deposited at the above depository on Feb. 24, 1982 under the terms of the Budapest Treaty.

*Saccharomyces cerevisiae* has the general properties mentioned below and the three diploid strains aforementioned above, namely, *Saccharomyces cerevisiae* FTY-3, *Saccharomyces cerevisiae* KB-3 and *Saccharomyces cerevisiae* FTY (FRI-413) have these characteristic properties.

| Fermentative ability of carbohydrates | |
|---|---|
| glucose | + |
| galactose | + |
| sucrose | + |
| maltose | + |
| lactose | − |
| Assimilation of carbon compounds | |
| glucose | + |
| galactose | + |
| sucrose | + |
| maltose | + |
| lactose | − |
| raffinose | + |
| soluble starch "Certified" (Lot. No. 0178-15, manufactured by Difco, Co. Ltd.) | + |
| Assimilation of nitrate ($KNO_3$) | − |
| Vitamin auxotrophy | |
| biotin | + |
| folic acid | − |
| nicotinic acid | − |
| thiamin | − |
| riboflavin | − |
| Ca-pantothenate | + |
| inositol | ± |
| pyridoxine | ± |
| p-aminobenzoic acid | − |

Separation of each haploid strain from the two parent strains is carried out by preculturing the parent strain each in a nutrient medium, inoculating the cells on a sporulation medium containing sodium acetate or potassium acetate, incubating the medium at 20° to 25° C. for 2 to 7 days until spores are formed, suspending the cells containing spores in a lyric enzyme solution and keeping the solution to incubate at 30° C. for 30 minutes to 1 hour. After the enzyme-treatment, spores are isolated from ascus using a micro manipulator. The spores isolated are transferred to the nutrient medium and cultured at 30° C. until germination is made and haploid strain is obtained. Each haploid strain is judged by testing whether or not conjugation occurs in the presence of a known mating type haploid strain.

Conjugation is conducted in such a manner as described in "Protein, Nucleic acid and Enzyme", Vol. 12, No. 12, pp. 1096–1099, Norio Gunke ed. (1967). Each haploid strain separated from the two parent strains is cultured in a nutrient medium at 30° C. for 4 to 8 hours, separately, and then, the same amount of the each cultured medium is mixed and the mixture is incubated at 30° C., to generate zygotes. The zygotes formed are isolated with a micro-manipulator and cultured. After several screenings of diploid hybrid strains having characteristics together of the parent strains, the present diploid hybrid strain *Saccharomyces cerevisiae* FTY-3 (FERM BP 2363) is obtained. The diploid hybrid strain was cultured with a fermenter and final product having water content of 64–73% was obtained after dehydration.

As mentioned above, the diploid hybrid strain according to the present invention is characterized by at east having strong fermentative ability of non-sugar dough and strong freeze-resistance. In particular, the diploid hybrid strain is distinguished from heretofore known diploid hybrid strains in having a non-freeze fermentative ability of not less than 140 ml and a residual fermentative ability rate after freezing of not less than 80%.

Herein, the term, "a non-freeze fermentative ability of not less than 140 ml", means that amount of carbon dioxide gas generated is not less than 140 ml when a strain is allowed to ferment at 30 °C. for 2 hours in a non-sugar dough. The diploid hybrid strain FTY-3 according to the present invention produces not less than 140 ml of carbon dioxide gas, which is useful for dough fermentation, in a non-sugar dough, and is distinguished from other known hybrid strains, for example, Saccharomyces species FD 612 strain (FERM BP-742), *Saccharomyces cerevisiae* KHI 110 strain (FERM BP-972) and *Saccharomyces cerevisiae* 3-2-6D strain (FERM BP-1235), by this characteristic.

Also, the term, "a residual fermentative ability rate after freezing of not less than 80%", means that the residual fermentative ability rate after freezing which is calculated from measurements of amounts of produced carbon dioxide gas in the case (non-freezing) where a strain is allowed to ferment at 30° C. for 60 minutes and subsequently, without freezing, at 38° C. for 60 minutes, and in the case (freezing) where a strain is allowed to ferment at 30° C. for 60 minutes, then frozen at −20° C. for 7 hours, thawed at 30° C. for 30 minutes, and allowed to ferment at 38° C. for 60 minutes, both using a non-sugar dough, is not less than 80%. The FTY-3 strain according to the present invention shows a residual fermentative ability rate of not less than 80%, and is distinguished from these known strains by this characteristic. As obvious from FIGS. 2 and 3, the FTY-3 strain according to the present invention seems to be of an enzyme-existence type and the other strains seem to be of an enzyme-induction type. In the FTY-3 strain, accordingly, enzymes which act for the utilization in the fermentation of maltose produced from injured starch in flours by the action of flour-originated amylase (namely, maltase and maltose permease), exist originally in the cells, while, in the other strains, these enzymes are induced in the cells during the course of fermentation.

In order to prepare the frozen dough, dough fomula such as flour, sugar, salt, fat, skim milk, egg, yeast food, yeast, water, etc., may be appropriately used. Sugar content in the dough is 0–20% by weight based on flour. The diploid hybrid strain *Saccharomyces cerevisiae* FTY-3 as described above is produced in the compressed form of a 70% water content, and then usually added to the dough in an amount of 1 to 10% by weight based on flour.

The preparation of frozen dough, for instance, for a white bread, is conducted by a straight dough method wherein steps are as follows: mixing and kneading all of flour and other ingredients together with yeast, floor time, dividing, rounding, bench, intermediate proof, molding and freezing, sequentially. In a sponge dough method, steps are mixing and kneading a part of flour and other ingredients together with yeast, the first fermentation to prepare a sponge, and mixing and kneading the sponge with remaining ingredients, floor time, dividing, rounding, bench, molding and freezing, sequentially. In the case of straight dough method, the floor time is set at 0 to 240 minutes and frozen at −15° to −40° C., usually under the ambient pressure. The bread which is produced using the frozen dough of the present invention is quite superior in apparency, specific volume, grain and flavor to the bread produced from frozen dough made with the common bakers' yeast.

The frozen dough of the present invention may be used for doughs of steamed pork buns, yeast doughnut and the like in addition to a variety of non-sugar dough having up to moderate sugar level for a white bread, French bread, bread crumb, buns or raisin bread.

The following examples explain the present invention but they are not intended to limit the present invention thereto.

EXAMPLE 1

Conjugation

Production of the present diploid hybrid strain, *Saccharomyces cerevisiae* FTY-3, (hereinafter referred to as a FTY-3 strain).

Step 1. Presporulation

Each of *Saccharomyces cerevisiae* KB-3 (FERM BP 2742) having strong fermentative ability of non-sugar dough and *Saccharomyces cerevisiae* FTY (FRI-413) (FERM BP 2743) having strong freeze-resistance, was inoculated on a YPD agar medium plate and precultured at 30° C. for 24 hours.

| Composition of YPD agar medium (pH 5.5) | |
|---|---|
| yeast extract (Lot. 012701, manufactured by Difco, Co. Ltd.) | 5 g |
| peptone (Lot 018802, manufactured by Difco, Co. Ltd.) | 10 g |
| glucose (special grade, manufactured by Wako Pure Chemical Industries, Ltd.) | 40 g |
| $KH_2PO_4$ (Lot. CTJ3919, manufactured by Wako Pure Chemical Industries, Ltd.) | 5 g |
| $MgSO_4.7H_2O$ (Lot. CTP2140, manufactured by Wako Pure Chemical Industries, Ltd.) | 2 g |
| agar (Lot. 014001, manufactured by Difco, Co. Ltd.) | 20 g |
| distilled water | 1000 ml |

Step 2. Sporulation

A loopful each of the two precultured strains was inoculated and cultured on Sherman's agar medium plate at 25° C. for 6 days to induce sporulation.

| Composition of Sherman's agar medium (pH 7.2) | |
|---|---|
| potassium acetate (special grade, manufactured by Wako Pure Chemical Industries, Ltd.) | 1.0 g |
| yeast extract (Lot. 012701, manufactured by Difco, Co. Ltd.) | 0.1 g |
| glucose (special grade, manufactured by Wako Pure Chemical Industries, Ltd.) | 0.05 g |
| agar (Lot. 014001, manufactured by Difco, Co. Ltd.) | 2.0 g |
| distilled water | 100 ml |

Step 3. Separation of spores

A loopful each of the two sporulated strains was suspended in a solution (2 ml) of a lytic enzyme (product name "Zymolyase-20T"; β-1, 3-glucan lamunaripentaohydrase; 2-3 U/ml, manufactured by KIRIN BREWERY, Co., Ltd.), respectively, and incubated at 30° C. for 30 minutes to 1 hour. After the enzyme treatment, spores were isolated from ascus with a micromanipulator.

Step 4. Germination and production of haploid strains

Each spore isolated was placed on the YPD agar medium plate and cultured at 30° C. until the spore germinated to produce a haploid strain. Mating types of strains were judged by testing whether or not conjugation appears in the presence of a known mating type haploid strains.

Step 5. Conjugation

Each haploid strain thus obtained, i.e. the haploid strain obtained from germination of the diploid yeast strain having strong fermentative ability of non-sugar dough and the haploid strain obtained from germination of spores of the diploid yeast strain having strong freeze-resistance, was separately cultured on the YPD medium, i.e., a medium having no agar in the YPD agar medium at 30° C. for 4 to 8 hours. Each cultured medium was mixed together and incubated at 30° C. until zygotes were produced. The zygotes formed were isolated with a micromanipulator and cultured. A colony was formed on an agar medium plate containing maltose as a sugar source and the same agar medium was over laid to have it fermented. A colony which was able to produce the largest amount of $CO_2$ therearound was selected, and was cultured in a liquid medium containing molasses as a sugar source. Cells obtained were frozen at $-20°$ C. for 7 days. Cells after being thawed were allowed to ferment in a liquid fermenting medium containing maltose as a sugar source and a strain which was able to produce the largest amount of $CO_2$ was selected. The selected cell was mixed with non-sugar dough to prepare frozen dough. The dough was thawed and a strain which was able to produce a large amount of $CO_2$ was selected.

Thus, the present diploid hybrid strain, Saccharomyces cerevisiae FTY-3 strain was obtained.

EXAMPLE 2

Fermentative Ability of Non-sugar Dough

Each strain was allowed to ferment in dough defined below at 30° C. for 2 hours and the $CO_2$ produced every 10 minutes for this period was measured as shown in the drawing attached.

| Composition of non-sugar dough | |
|---|---|
| flour (NISSHIN SEIFUN, Japan trademark "Camelia" (bread making protein flour) | 20 g |
| salt | 0.3 g |
| yeast | 0.4 g |
| water (Shizuoka prefecture, Ohito-cho) | 13 ml |

TABLE 1

| | $CO_2$ production |
|---|---|
| ordinary bakers' yeast | 78 ml |
| yeast for non-sugar dough | 152 ml |
| FTY-3 strain | 161 ml |
| freeze-resistant yeast | 82 ml |

TABLE 1-continued

| | $CO_2$ production |
|---|---|
| FTY (FRI 413) | 32 ml |

Notes:
*Ordinary baker's yeast: Saccharomyces cerevisiae 237NG (product name "45 Yeast", manufactured by Toyo Jozo Co., Ltd.).
*Yeast for non-sugar dough; Sacharomyces cerevisiae KB-3 (FERM BP 2742) (product name "45 Red Yeast", manufactured by Toyo Jozo Co., Ltd.).
*Freeze-resistant yeast; a product marketed in Japan.
*FTY (FRI 413); Saccharomyces cerevisiae FTY (FRI-413) (FERM BP 2743).

The same was applied to hereinafter.

EXAMPLE 3

Fermentative Ability of Non-sugar Dough and Dough with a Moderate Sugar Level

Each strain was fermented in two varieties of dough with the following composition, i.e. dough with a low sugar level (sugar content, 5% based on flour) and dough with a moderate sugar level (sugar content, 20% based on flour) at 30° C. for 2 hours. $CO_2$ produced for this period was measured as shown in Table 2.

| | Composition | |
|---|---|---|
| | Dough with a low sugar level | Dough with a moderate sugar level |
| flour (same above) | 20 g | 20 g |
| salt | 0.3 g | 0.3 g |
| sugar | 1 g | 4 g |
| yeast | 0.4 g | 0.4 g |
| water (same above) | 12.4 ml | 10 ml |

TABLE 2

| | $CO_2$ production in dough with a low sugar level | $CO_2$ production in dough with a moderate sugar level |
|---|---|---|
| ordinary bakers' yeast | 125 ml | 220 ml |
| yeast for non-sugar dough | 132 ml | 195 ml |
| FTY-3 strain | 136 ml | 215 ml |
| freeze-resistant yeast | 120 ml | 200 ml |

A strain FTY-3 showed weaker fermentative ability in dough with a high sugar level than in non-sugar dough and dough with a moderate sugar level.

EXAMPLE 4

Freeze-resistance (Non-sugar Dough)

The non-sugar dough shown in Example 2 was fermentated at 30° C. for 60 minutes and frozen at $-20°$ C. for 7 days. After being thawed at 30° C. for 30 minutes, the resulting dough was fermentated at 38° C. for 60 minutes and $CO_2$ produced was measured as shown in Table 3.

TABLE 3

| | $CO_2$ production before freezing | $CO_2$ production after thawing |
|---|---|---|
| ordinary bakers' yeast | 85 ml | 35 ml |
| yeast for non-sugar dough | 105 ml | 40 ml |
| FTY-3 strain | 108 ml | 88 ml |
| freeze-resistant | 82 ml | 65 ml |

TABLE 3-continued

| | $CO_2$ production before freezing | $CO_2$ production after thawing |
|---|---|---|
| yeast | | |

EXAMPLE 5

Freeze-resistance (Dough with a Low Sugar Level)

The dough with a low sugar level shown in Example 3 was fermentated at 30° C. for 60 minutes and frozen at −20° C. for 7 days. After being thawed at 30° C. for 30 minutes, the resulting dough was fermented at 30° C. for 120 minutes. $CO_2$ produced in the latter fermentation was measured as shown in Table 4.

TABLE 4

| | $CO_2$ production before freezing | $CO_2$ production after thawing |
|---|---|---|
| ordinary bakers' yeast | 140 ml | 42 ml |
| yeast for non-sugar dough | 150 ml | 45 ml |
| FTY-3 strain | 154 ml | 118 ml |
| freeze-resistant yeast | 142 ml | 85 ml |

EXAMPLE 6

Shelf Life of Yeast $CO_2$ produced on the bakers' yeast for non-sugar dough was measured and that of a strain FTY-3, immediately after production thereof and after 4 days storage at 25° C. The results are shown in Table 3.

TABLE 5

| | $CO_2$ production immediately after production | $CO_2$ production after storage |
|---|---|---|
| yeast for non-sugar dough | 150 ml | 90 ml |
| FTY-3 strain | 161 ml | 142 ml |

EXAMPLE 7

Sporulation and Germination Ratio

Each loopful strain as in Example 2 was thinly inoculated on the YM agar medium plate (10 ml per sterilized petri dish of 85 mm diameter) using a flame-sterilized loop and precultured at 30° C. for 24 hours. The resulting each strain was again thinly inoculated on the Sharman's agar medium plate (10 ml per sterilized petri dish of 85 mm diameter) using a flame-sterilized loop and incubated at 25° C. for 7 days.

The strain each was subsequently stained according to the Möller's method in "Classification and Identification of Yeast", pp. 17–18, Hiroshi Iizuka and Shoji Goto ed., published by Tokyo University Press, on Mar. 21, 1969. The number of sporulating ascus every 100 cells was measured under a microscope.

Loopful cells each having sporulation ascus were suspended in a filtered solution (2 ml) of a lyric enzyme (3 mg/ml Zymolyase-20T in 0.05M Tris-HCl buffer, pH 7.5), in a sterilized tube (18 mm diameter). The tubes were incubated at 30° C. for 1 hour and centrifugated (3000 rpm) for 10 minutes. The obtained cells were washed twice with sterilized water and suspended in 2 ml of sterilized water.

Spores were isolated from the enzyme-treated cells with a micromanipulator and germinated at 30° C. on the YNB agar medium plate, a synthetic medium for yeasts. One hundred spores were separated from asci having 4 spores each inside.

| YM agar medium (pH 5.6) | |
|---|---|
| Yeast extract (Lot. 012701, manufactured by Difco, Co. Ltd.) | 0.3 g |
| glucose (special grade, manufactued by Wako Pure Chemical Industries, Ltd.) | 1.0 g |
| maltose extract (Lot. 0186015, manufactured by Difco, Co. Ltd.) | 0.3 g |
| peptone (Lot. 018802, manufactured by Difco, Co. Ltd.) | 0.5 g |
| agar (Lot. 014001, manufactured by Difco, Co. Ltd.) | 2.0 g |
| distilled water | 100 ml |

YNB agar medium (pH 5.6)

(Bacto-Yeast Nitrogen base in "Genetic experimental series, Vol. 3, Microbiological genetics research technique", pp. 186–188, Tatsuo Ishikawa ed., published by Kyoritsu Press, Japan, on Mar. 10, 1982).

| YEAST NITROGEN BASE (Lot. 760960, manufactured by Difco, Co. Ltd.) | 0.67 g |
|---|---|
| glucose (special grade, manufactured by Wako Pure Chemical Industries, Ltd.) | 2.0 g |
| agar (Lot. 014001, manufactured by Difco, Co. Ltd.) | 2.0 g |
| distilled water | 100 ml |

The sporulation ratio and germination ratio of spores obtained above are shown in Table 6.

TABLE 6

| Strain | Sporulation ratio (%) | Germination ratio (%) |
|---|---|---|
| ordinary bakers' yeast | 2 | 4 |
| yeast for non-sugar dough | 20 | 10 |
| FTY-3 strain | 14 | <1 |
| freeze-resistant yeast | 12 | 5 |
| FTY (FRI 413) | 2 | 8 |

The FTY-3 strain of the present invention as described above showed a characteristic that its germination ratio of spores was so small in the YNB agar medium plate, a synthetic medium for yeasts, that the strain could be identified from other strains.

EXAMPLE 8

Serological Characteristic of FTY-3 Strain

Rabbit antisera generated against FTY-3 strain as antigen were immunologically examined in relation to each yeast strain as in Example 2.

The preparation of antigen and antibody and that of specific antibody absorpted with yeast strains (237 NG, KB-3, FTY-3 strain) were explained hereinafter. The agglutination was assayed as in the following.

Antigen: FTY-3 strain was suspended in physiological saline to a final concentration of about $10^{10}$ cells/ml and heated at 80° C. for 30 minutes followed by centrifugation (1000 rpm) for 5 minutes to obtain 50 ml of the supernatant.

Antibody: Japanese white 5 rabbits aged 6 weeks were each injected 1 ml of the above antigen solution through ear vein using injectors. Additionally, 2 ml and 5 ml of the antigen solution were injected once and three times, respectively, with 4 days interval. On 8th day from the final immunization, blood was taken from the carotid artery of each rabbit. Whole blood was centrifuged (3000 rpm) for 15 minutes to yield about 20 ml of antiserum from each rabbit. Saturated ammonium sulfate solution (5 ml) was added to each antiserum (10 ml), and the mixture was kept at 5° C. overnight and was centrifuged (5000 rpm) for 15 minutes. After each precipitated γ-globulin was dissolved and dialyzed against physiological saline, it was adjusted to a final protein concentration of 20 mg/ml and designated as an antibody solution (A).

Specific antibody preparations absorbed with 237NG, KB-3 or FTY-3 strain: The ordinary bakers' yeast (300 mg each, Saccharomyces cerevisiae 237NG) was added to antibody solutions (A) (2 ml each), and reaction was allowed to proceed at 5° C. for 15 minutes. Supernatant obtained by centrifugation of the reaction solution was subjected to agglutination with the ordinary bakers' yeast Saccharomyces cerevisiae 237NG This process was repeated until no agglutination was observed. Subsequently, the resulting antibody solution was diluted with physiological saline to a final protein solution of 10 mg/ml (B).

Yeast (Saccharomyces cerevisiae KB-3) for non-sugar dough was used in place of the ordinary bakers' yeast to carry out the above procedure similarly. The resulting solution was adjusted to a protein solution of 10 mg/ml (C).

Furthermore, the antibody solution (C) was subjected to an absorption treatment with FTY-3 strain, and then, the protein concentration of the resulting antibody solution was adjusted to 10 mg/ml (D).

Procedures for agglutination test: Each of the yeast cells was suspended in physiological saline to a concentration of about $10^9$ cells/ml. The suspension was divided to 40 μl each per well of 96-well microtiter plates. Each antibody solution (A) or any one of antibody solutions (B) through (D) was added to wells at a volume of 40 μl, separately, and shaken for 5 minutes. After these wells were kept to stand for 30 minutes, each well was examined in terms of the presence or absence of an agglutination mass. Tables 7, 8, 9 and 10 show the results of agglutination test using the antibody solution without absorption with yeast (A), the antibody solutions (B), (C) and (D), respectively. Normal serum shown in tables represents the serum from rabbits with no treatment.

TABLE 7

(A)

| Sample | Antibody solutions | | | | | Normal serum |
|---|---|---|---|---|---|---|
| | 1 | 2 | 3 | 4 | 5 | |
| ordinary bakers' yeast | + | + | + | + | + | − |
| yeast for non-sugar dough | + | + | + | + | + | − |
| FTY-3 strain | + | + | + | + | + | − |
| freeze-resistant yeast | + | + | + | + | + | − |
| FTY (FRI 413) | + | + | + | + | + | − |

TABLE 8

(B)

| Sample | Antibody solutions | | | | | Normal serum |
|---|---|---|---|---|---|---|
| | 1 | 2 | 3 | 4 | 5 | |
| ordinary bakers' yeast | − | − | − | − | − | − |
| yeast for non-sugar dough | − | + | + | − | − | − |
| FTY-3 strain | − | + | + | + | − | − |
| freeze-resistant yeast | − | − | − | − | − | − |
| FTY (FRI 413) | − | + | + | + | − | − |

TABLE 9

(C)

| Sample | Antibody solutions | | | | | Normal serum |
|---|---|---|---|---|---|---|
| | 1 | 2 | 3 | 4 | 5 | |
| ordinary bakers' yeast | − | − | − | − | − | − |
| yeast for non-sugar dough | − | − | − | − | − | − |
| FTY-3 strain | − | + | + | + | + | − |
| freeze-resistant yeast | − | − | − | − | − | − |
| FTY (FRI 413) | − | + | + | + | − | − |

TABLE 10

(D)

| Sample | Antibody solutions | | | | | Normal serum |
|---|---|---|---|---|---|---|
| | 1 | 2 | 3 | 4 | 5 | |
| ordinary bakers' yeast | − | − | − | − | − | − |
| yeat for non-sugar dough | − | − | − | − | − | − |
| FTY-3 strain | − | − | − | + | + | − |
| freeze-resistant yeast | − | − | − | − | − | − |
| FTY (FRI 413) | − | − | − | − | − | − |

Example 9 Baking test
1 French bread

| Composition | |
|---|---|
| flour (same above) | 100 g |
| yeast | 4 g |
| yeast foods (Toyo Jozo, trade name "Amila") | 0.1 g |
| malt extract (SANKYO FOODS, Japan, trade name "Sankyo Malt Ekisu $B_2$") | 0.3 g |
| salt | 2 g |
| water (same above) | 63 ml |

| Procedure (Straight dough method) | |
|---|---|
| fermentation time | 60 min. |
| dividing | 100 g |
| bench time | 20 min. |
| freezing after molding at −20° C. | |
| thawing 30° C., | 60 min. |
| proofing 20° C., | 60 min. |
| baking 230° C., | 15 min. |

TABLE 11

| | Bread volume | | |
|---|---|---|---|
| | non-freezing | frozen for 7 days | frozen for 14 days |
| yeast for non-sugar dough | 350 ml | 270 ml | 250 ml |
| FTY-3 strain | 360 ml | 310 ml | 300 ml |
| freeze-resistant yeast | 310 ml | 280 ml | 275 ml |

2 A white bread (sugar content: 5% based on flour)

| Composition | |
|---|---|
| flour (same above) | 100 g |
| yeast | 4 g |
| yeast foods (same above) | 0.1 g |
| fat | 5 g |
| sugar | 5 g |
| salt | 2 g |
| water (same above) | 65 ml |
| Procedure (straight dough method) | |
| fermentation time | 40 min. |
| dividing | 50 g |
| freezing after molding at −20° C. | |
| thawing 30° C., | 90 min. |
| proofing 38° C., | 40 min. |
| baking 200° C., | 35 min. |

TABLE 12

| | Bread volume | | |
|---|---|---|---|
| | non-freezing | frozen for 7 days | frozen for 14 days |
| yeast for non-sugar dough | 285 ml | 180 ml | 145 ml |
| FTY-3 strain | 290 ml | 265 ml | 230 ml |
| freeze-resistant yeast | 280 ml | 230 ml | 195 ml |

3 Butter roll (sugar content: 10% based on flour)

| Composition | |
|---|---|
| flour (same above) | 100 g |
| yeast | 4 g |
| yeast foods (same above) | 0.1 g |
| fat | 10 g |
| sugar | 10 g |
| whole egg | 10 g |
| salt | 1.5 g |
| water (same above) | 48 ml |
| Procedure (straight dough method) | |
| fermentation time | 45 min. |
| dividing | 50 g |
| first bench time | 10 min. |
| second bench time | 10 min. |
| molding | |
| freezing after molding at −20° C. | |
| thawing 30° C., | 30 min. |
| proofing 38° C., 80 % humidity, | 40 min. |
| baking 200° C., | 10 min. |

TABLE 13

| | Bread volume | | |
|---|---|---|---|
| | non-freezing | frozen for 7 days | frozen for 14 days |
| yeast for non-sugar dough | 255 ml | 185 ml | 130 ml |
| FTY-3 strain | 270 ml | 255 ml | 240 ml |
| freeze-resistant yeast | 250 ml | 220 ml | 170 ml |

4 Buns (sugar content: 15% based on flour)

| Composition | |
|---|---|
| flour (same above) | 100 g, |
| skim milk | 3 g |
| yeast | 4 g |
| whole egg | 8 g |
| yeast food (same above) | 0.1 g |
| fat | 8 g |
| sugar | 15 g |
| salt | 1.3 g |
| water (same above) | 50 ml |
| Procedure (straight dough method) | |
| fermentation time | 40 min. |
| dividing | 50 g |
| bench time | 15 min. |
| freezing after molding at −20° C. | |
| thawing 30° C., | 30 min. |
| proofing 38° C., | 50 min. |
| baking 200° C., | 10 min. |

TABLE 14

| | Bread volume | | |
|---|---|---|---|
| | non-freezing | frozen for 7 days | frozen for 14 days |
| yeast for non-sugar dough | 280 ml | 250 ml | 240 ml |
| FTY-3 strain | 282 ml | 278 ml | 273 ml |
| freeze-resistant yeast | 270 ml | 265 ml | 260 ml |

5 Buns (sugar content: 20% based on flour)

| Composition | |
|---|---|
| flour (same above) | 100 g, |
| skim milk | 3 g |
| yeast | 5 g |
| whole egg | 8 g |
| yeast food (same above) | 0.1 g |
| fat | 8 g |
| sugar | 20 g |
| salt | 1.3 g |
| water (same above) | 48 ml |
| Procedure (straight dough method) | |
| fermentation time | 60 min. |
| dividing | 50 g |
| bench time | 15 min. |
| freezing after molding at −20° C. | |
| thawing 30° C. | 30 min. |
| proofing 38° C. | 50 min. |
| baking 200° C. | 10 min. |

TABLE 15

| | Bread volume | | |
|---|---|---|---|
| | non-freezing | frozen for 7 days | frozen for 14 days |
| yeast for non-sugar dough | 300 ml | 265 ml | 242 ml |
| FTY-3 strain | 293 ml | 292 ml | 290 ml |
| freeze-resistant yeast | 276 ml | 270 ml | 265 ml |

EXAMPLE 10

Comparative Tests on the FTY-3 Strain with Other Strains for the Freeze-resistance in a Non-sugar Dough Non-freeze and after-freeze fermentative abilities of the present FTY-3 strain in a non-sugar dough were compared with those of other heretofore known hybrid strains, i.e., *Saccharomyces species* FD 612 (FERM BP-742) (hereinafter referred to as FD 612), *Saccharomyces cerevisiae* KFI 110 (FERM BP-972) (hereinafter referred to as KFI 110) and *Saccharomyces cerevisiae* 3-2-6D (FERM BP-1235) (hereinafter referred to as 3-2-6D), as well as an ordinary bakers' yeast strain (237 NG: non-freeze-resistant strain) and a commercially available freeze-resistant yeast strain used for frozen dough (TFD-1).

Each of the strains was cultured as follows:

| YPD liquid medium composition (pH 5.5) | |
|---|---|
| Yeast extract (manufactured by Difco Co., Ltd., Lot 013402) | 5 g |
| Peptone (manufactured by Difco Co., Ltd., Lot 020408) | 10 g |
| Glucose (manufactured by Wako Pure Chemical Indutries, Ltd., special grade) | 40 g |
| $KH_2PO_4$ (manufactured by Wako Pure Chemical Industries, Ltd., Lot CTJ 3919) | 5 g |
| $MgSO_4.7H_2O$ (manufactured by Wako Pure Chemical Industries, Ltd., Lot CTP 2340) | 2 g |
| Distilled water | 1000 ml |
| Molasses medium (pH 5.6) | |
| Molasses (product from the Philippines, sugar content 35%) | 120 ml |
| $KH_2PO_4$ (manufactured by Wako Pure Chemical Industries, Ltd., Lot CTJ 3919) | 0.4 g |
| Urea (manufactured by JUNSEI KAGAKU KABUSHIKI KAISHA, special grade, Lot 3D1075) | 2.8 g |
| $(NH_4)_2SO_4$ (manufactured by Wako Pure Chemical Industries, Ltd., special grade, Lot CTJ 3814) | 1 g |
| $MgSO_4.7H_2O$ (manufactured by KANTO KAGAKU KABUSHIKI KAISHA, special grade, Lot 205A5993) | 0.3 g |
| Distilled water | 880 ml |

To 5 ml of the above YPD liquid media (in a $\phi$ 16 mm × 105 mm test tube) was inoculated a loopful each strain from a slant culture, and the medium was subjected to a shaken culture at 30° C. for 24 hours.

One milliliter of the cultured medium was inoculated to 100 ml of the above molasses medium (in a 500 ml-volume Erienmeyer flask), and the medium was subjected to a shaken culture at 30° C. for 48 hours.

The cultured medium was subjected to a centrifugation under 3000 rpm for 10 minutes to collect the cells. After rinsing under the same conditions, the cells (containing 67% water) were obtained by pressing dehydration using a filter paper.

| Non-sugar dough composition | |
|---|---|
| Flour (manufactured by NISSHIN SEIFUN KABUSHIKI KAISHA, "Camelia", a bread making protein flour) | 20 g |
| Table salt | 0.3 g |
| Yeast | 0.4 g |
| Water | 13 ml |

The cells were added to the above non-sugar dough, and the dough was subjected to a mixing for 2 minutes. A divided 33.7 g (20 g as flour) portion of the dough was allowed to ferment at 30° C. for 60 minutes. After degasification the dough was frozen at −20° C. for 7 days. After being thawed at 30° C. for 30 minutes, the dough was allowed to ferment at 38° C. for 60 minutes, and the amount of gas generated was measured by a fermograph.

① Non-freeze fermentative ability

Each strain was allowed to ferment at 30° C. for 2 hours in the non-sugar dough (without freezing), the amount of carbon dioxide gas generated was measured. The results are comparatively shown in Tables 16 and 17 below.

TABLE 16

| Strains | Amount of gas generated |
|---|---|
| FTY-3 | 153 ml |
| KFI 110 | 71 ml |
| FD 612 | 48 ml |
| 237 NG | 73 ml |
| TFD-1 | 79 ml |

TABLE 17

| Strains | Amount of gas generated |
|---|---|
| FTY-3 | 156 ml |
| 3-2-6D | 81 ml |
| 237 NG | 75 ml |
| TFD-1 | 78 ml |

As obvious from the tables, the present FTY-3 strain exhibited a strong fermentative ability in non-sugar dough composition as shown from the amount of generated gas of not less than 140 ml, which is useful for dough fermentation. While, the known strains, KFI 110 and FD 612, exhibited far less amount of the gas as compared with the FTY-3 strain, even lower than that of the commercially available freeze-resistant TFD-1 strain. The 3-2-6D strain exhibited less amount of the gas as compared with the FTY-3 strain, showing the similar fermentative ability to that of the TFD-1 strain.

② Every 10 minutes gas generation in non-freeze fermentation

Each strain was allowed to ferment in the non-sugar dough at 30° C. for 2 hours, and the amounts of gas generated every 10 minutes were measured with curves as shown in FIGS. 2 and 3.

The present FTY-3 strain exhibited a curve in which the amounts of gas generated gradually increased from the beginning of fermentation to after 50 minutes, and thereafter reached to a steady level, showing an enzyme-existence pattern. While, the curves from the KFI 110, FD 612 and 3-2-6D strains exhibited peaks of the gas amounts after about 30 minutes, then decreases and again increases after about 60 minutes, showing an enzyme-induction pattern which is similar to the 237 NG and TFD-1 strains.

③ Residual fermentative ability after freezing

In the case of non-freezing, each strain was allowed to ferment in the non-sugar dough at 30° C. for 60 minutes, and subsequently (without freezing) allowed to ferment at 38° C. for 60 minutes. In the case of freezing, each strain was allowed to ferment in the non-sugar dough at 30° C. for 60 minutes, then the dough was frozen at −20° C. for 7 days and thawed at 30° C. for 30 minutes and then (after freezing) allowed to ferment at 38° C. for 60 minutes. The amounts of carbon dioxide gas generated in both cases at the second fermentation were measured with the results shown in Tables 18 and 19.

TABLE 18

| Strains | Gas generated (non-freeze) | Gas generated (after freezing) | Residual fermentative ability rate |
|---|---|---|---|
| FTY-3 | 101 ml | 84 ml | 83.2% |
| KFI 110 | 73 ml | 44 ml | 60.3% |
| FD 612 | 53 ml | 41 ml | 77.4% |
| 237 NG | 80 ml | 33 ml | 41.3% |
| TFD-1 | 81 ml | 60 ml | 74.1% |

TABLE 19

| Strains | Gas generated (non-freeze) | Gas generated (after freezing) | Residual fermentative ability rate |
|---|---|---|---|
| FTY-3 | 103 ml | 86 ml | 83.5% |
| 3-2-6D | 82 ml | 58 ml | 70.7% |
| 237 NG | 78 ml | 31 ml | 39.7% |
| TFD-1 | 80 ml | 57 ml | 71.3% |

It is obvious from the tables that the present FTY-3 strain is an excellent freeze-resistant strain at least having a residual fermentative ability rate of not less than 80%. While, the known KFI 110 strain exhibited a far less amount of gas generated after freezing, as compared with that of the FTY-3 strain. Also, the known FD 612 strain exhibited far less amounts of gas generated both in non-freezing and after freezing, showing an insufficient fermentative ability to be used for producing non-sugar dough breads. Further, the known strains exhibited lower gas generation amounts in non-freezing and after freezing, when compared with those of the commercially available freeze-resistant TFD-1 strain. The known 3-2-6D strain exhibited a residual fermentative ability rate of as low as 70.7%, although it showed the similar degree of gas amounts generated in a non-freeze condition and after freezing as those of the commercially available TFD-1 strain.

As seen from the results of the above comparative tests, the FTY-3 strain according to the present invention is definitely superior to the other known strains, KFI 110, FD 612 and 3-2-6D, in each of its non-freeze fermentative ability, every 10 minutes gas generation in non-freeze fermentation, and residual fermentative ability after freezing. Accordingly, the present FTY-3 strain is distinguished from them in its characteristics of having a non-freeze fermentative ability of not less than 140 ml and a residual fermentative ability rate after freezing of not less than 80%, in a non-sugar dough.

According to the present invention, high-quality frozen bread dough having non-sugar for French bread and bread crumb and white bread having up to a moderate sugar level (sugar content: 0 to 20% based on flour) may be provided.

Furthermore, non-sugar dough containing the diploid hybrid strain according to the present invention has longer storage life than the same dough containing the conventional yeasts. Accordingly, the present yeast or dough containing the same is convenient when stored or transported.

We claim:

1. A diploid hybrid yeast strain produced by the process comprising the following steps:
    (1) germinating the spores of:
        (a) a first diploid strain of *Saccharomyces cerevisiae* which has a non-freeze fermentative ability on non-sugar dough of at least 140 ml, and
        (b) a second diploid strain of *Saccharomyces cerevisiae* which has a residual fermentative ability rate on non-sugar dough of at least 80%;
    (2) recovering haploid yeast strains from said germinated first and second diploid strains, respectively; and
    (3) conjugating said haploid yeast strains to provide a diploid hybrid yeast strain having a non-freeze fermentative ability on non-sugar dough of at least 140 ml and a residual fermentative ability rate, using non-sugar dough, of at least 80%, wherein said diploid hybrid yeast strain is a biologically pure culture of *Saccharomyces cerevisiae* having all the identifying characteristics of FTY-3 (FERM BP-2326).

2. The diploid hybrid yeast strain as claimed in claim 1, wherein said first diploid strain is *Saccharomyces cerevisiae* KB-3 (FERM BP 2742).

3. The diploid hybrid yeast strain as claimed in claim 1, wherein said second diploid strain is *Saccharomyces cerevisiae* FTY (FRI-413) (FERM BP 2743).

4. The diploid hybrid yeast strain as claimed in claim 1, wherein said non-sugar dough comprises up to 20% by weight of sugar, based on the flour content of said dough.

5. A diploid hybrid yeast strain having fermentative ability on non-sugar bread dough and freeze resistance, produced by the steps comprising:
    (1) germinating the spores of the following two yeast strains:
        (a) a first diploid strain of *Saccharomyces cerevisiae* which has a non-freeze fermentative ability on non-sugar dough of at least 140 ml, wherein said non-freeze fermentative ability is qualified by measuring the amount of carbon dioxide generated when the first diploid strain is allowed to ferment non-sugar dough for 2 hours at 30° C., and
        (b) a second diploid strain of *Saccharomyces cerevisiae* which has a residual fermentative ability rate on non-sugar dough of at least 80%, wherein said residual fermentative ability rate is quantified by preparing a first and second batch of non-sugar dough containing the second yeast strain, said batches being equivalent, fermenting said first and second batches at 30° C. for 60 minutes, freezing said second batch at −20° C. for 7 days and then thawing at 30° C. for 30 minutes, fermenting said first and second batches at 38° C. for 60 minutes and measuring the carbon dioxide generated for each batch;
    (2) recovering haploid yeast strains from said germinated first and second diploid strains, respectively;
    (3) conjugating said haploid yeast strains; and
    (4) selecting from said conjugation a diploid hybrid yeast strain having a non-freeze fermentative ability on non-sugar dough of at least 140 ml and a residual fermentative ability rate, using non-sugar dough, of at least 80%, wherein said diploid hybrid yeast strain is a biologically pure culture of *Saccharomyces cerevisiae* having all the identifying characteristics of FTY-3 (FERM BP-2326).

6. The diploid hybrid yeast strain as claimed in claim 5, wherein said non-sugar dough comprises up to 20% by weight of sugar, based on the flour content of said dough.

7. A biologically pure culture of *Saccharomyces cerevisiae* having all the identifying characteristics of FTY-3 (FERM BP-2326).

8. A bread dough appropriate for freezing comprising a dough formula and the diploid hybrid yeast strain according to claim 5.

9. The bread dough according to claim 8 comprising up to 20% sugar based on flour in said dough formula.

* * * * *

UNITED STATES PATENT AND TRADEMARK OFFICE
CERTIFICATE OF CORRECTION

PATENT NO. : 5,352,606
DATED : October 4, 1994
INVENTOR(S) : HIROYUKI TAKANO, AKIHIRO HINO, HISANORI ENDO
NOBUAKI NAKAGAWA, AKIO SATO It is certified that error appears in the above-indentified patent and that said Letters Patent is hereby corrected as shown below:

On the Title Page, item [73], insert the following information:

--and National Food Research Institute, Ministry of Agriculture, Forestry and Fisheries, Ibaraki, Japan--.

Signed and Sealed this

Twenty-eight Day of February, 1995

Attest:

BRUCE LEHMAN

*Attesting Officer*          *Commissioner of Patents and Trademarks*